United States Patent [19]

Snow et al.

[11] Patent Number: 4,472,502

[45] Date of Patent: Sep. 18, 1984

[54] MALOLACTIC GENE

[75] Inventors: Sidney R. Snow; Ralph E. Kunkee; Robert A. Hodges; Steven A. Williams, all of Davis, Calif.

[73] Assignee: The Regents of the University of California, Berkeley, Calif.

[21] Appl. No.: 408,555

[22] Filed: Aug. 16, 1982

[51] Int. Cl.$^3$ ............... C12N 1/18; C12N 15/00; C12N 5/00; C12N 1/20; C12N 1/16; C07H 21/04

[52] U.S. Cl. ............... 435/172.3; 435/256; 435/240; 435/253; 435/255; 536/27; 935/16; 935/66; 935/69; 935/72; 935/73

[58] Field of Search ............... 435/68, 70, 91, 172, 435/253, 255, 256, 317, 172.3; 536/27

[56] References Cited

U.S. PATENT DOCUMENTS 4,387,162 6/1983 Aigle et al. ............... 435/256

FOREIGN PATENT DOCUMENTS 2068969 8/1981 United Kingdom ............... 435/172

OTHER PUBLICATIONS

Schutz and Radler, *Arch. Mikrobiol.* (1973), 91:183-202, Abstract Only.

Schutz and Radler, *Arch. Mikrobiol.* (1974), 96:329-339, Abstract Only.

Buchanan et al.: *Bergey's Manual of Determinative Bacteriology*-8th Edition, 1974, Williams & Wilkins Co., pp. 513-515.

Botstein et al.: Recombinant DNA Technicla Bulletin 2, 49, (1979).

Struhl et al.: Proc. Natl. Acad. Sci. U.S.A. 76, 1035, (1979).

Subden et al.: Abstract of Can. J. Microbiol. 28(7), 883, (1982).

*Primary Examiner*—Lionel M. Shapiro
*Assistant Examiner*—James Martinell
*Attorney, Agent, or Firm*—Townsend and Townsend

[57] ABSTRACT

DNA sequences which are capable of converting L-malate into L-lactate are incorporated into suitable vectors and used to transform both prokaryotic and eukaryotic hosts. The DNA sequences and vectors are particularly useful in conferring the ability to perform malolactic fermentation on wine producing yeasts.

*Saccharomyces cerevisiae* 2514-10C/ySW1 and *E. coli* RRI/ySW1 were deposited at the A.T.C.C. on Aug. 16, 1982, and given accession Ser. Nos. 20651 and 39176, respectively.

11 Claims, No Drawings

MALOLACTIC GENE

BACKGROUND OF THE INVENTION

1. Field of the Invention

Malolactic fermentation is a secondary fermentation that occurs in addition to the primary alcoholic fermentation in the production of many wines. The reaction, the decarboxylation of L-malic acid to L-lactic acid, is carried out only by certain species of the genera Lactobacillus, Pediococcus, and Leuconostoc. Malic acid is the major organic acid found in grapes and its decarboxylation to lactic acid results in a significant decrease in the acidity of the wine, which is a matter of some importance in cool grape growing regions where the grape must may be too acidic. Malolactic fermentation also provides bacteriological stability. Once the malolactic fermentation has been completed in wine, no other microbial fermentations occur and this prevents spoilage. The latter is the most important attribute of the malolactic fermentation. A less important attribute is the subtle influence that malolactic fermentation may have on the flavor complexity of the wine.

Malolactic fermentation usually occurs after several months of storage of the wine. This late onset can result in off flavors, and turbidity if it occurs after bottling. The fermentation is slow due to many factors. The initial inoculum is usually small, and more importantly the enviroment of wine is usually not conducive to rapid growth of the malolactic fermenting bacteria. The ethanol and sulfur dioxide concentrations are too high, and the pH, nutrient concentrations and the temperature are too low for optimal growth of these bacteria.

Winemakers often stimulate malolactic fermentation, when it is desirable, through a variety of means. A large inoculum with a lactic acid bacterial strain found to grow with reliability in wine is helpful. Delayed removal of the wine from the yeast sediment, delay in the addition of acidifying agents, low sulfur dioxide concentration, lack of filtration of the wine, and warmer temperatures all encourage malolactic fermentation. These same conditions, however, also encourage spoilage of the wine by other bacteria and yeast species. To prevent such spoilage of wine, it would be desirable to have the malolactic fermentation occur during or shortly after the alcoholic fermentation. The wine could then be adjusted for cellar storage and bottling with no risk of spoilage.

There are a limited number of ways such rapid malolactic fermentation could be induced. Winemakers could add increased dosages of inoculum to induce the fermentation, but such large fermentations would require vast amounts of starter culture. Enzymes isolated from lactic acid bacteria could be used instead of the malolactic fermenting bacteria themselves, but obtaining the enzymes would be difficult and very expensive.

It would thus be desirable to identify and isolate a gene which is able to confer the ability to decarboxylate L-malic acid to L-lactic acid in a suitable host. By introducing this trait to a yeast host capable of fermenting wines, malolactic fermentation could be carried out simultaneously with primary alcoholic fermentation in the production of many wines.

2. Description of the Prior Art

Schutz and Radler (1973) Arch. Mikrobiol. 91:183-202 and Schutz and Radler (1974) Arch. Mikrobiol. 96: 329-339 have purified the malolactic enzyme and report a molecular weight of 150,000 in *Lactobacillus plantarum* and of 130,000 to 140,000 in *Leuconostoc mesenteroides*.

SUMMARY OF THE INVENTION

DNA sequences expressing polypeptides having the ability to decarboxylate L-malate to L-lactate are provided. Vectors incorporating the DNA sequences are used to transform susceptible hosts. Transformed yeasts are utilized in the production of wine where malolactic fermentation occurs substantially simultaneously with primary alcoholic fermentation.

DESCRIPTION OF THE SPECIFIC EMBODIMENTS

The DNA sequences of the present invention comprise the structural gene encoding for the malolactic enzyme, as well as various derivatives of the structural gene which are incorporated into vectors useful in transforming susceptible hosts.

The DNA sequence encoding the malolactic enzyme, referred to herein as the malolactic or the ML gene, is less than about 5 kbp and can be derived directly or indirectly from chromosomal DNA of various malolactic bacteria, including certain species of Leuconostoc such as *L. oenos* and *L. mesenteroides;* Lactobacillus such as *L. delbrueckii, L. leichmannii, L. acidophillus, L. casei, L. plantarum, L. fermenti, L. brevis, L. buchneri, L. hilgardii,* and *L. trichodes;* and Pediococcus such as *P. cerevisiae* and *P. pentosaceus.*

The ML gene may be isolated from the chromosomal DNA of an appropriate strain of malolactic bacteria by conventional techniques. Typically, high molecular weight DNA is obtained by first lysing the cell in a detergent, such as sodium dodecyl sulfate, which denatures and inactivates the DNAses. The proteins may then be extracted in an organic solvent, typically phenol, and the RNA may be separated by buoyant density centrifugation. Alternatively, the nucleic acids may be concentrated by ethanol precipitation and the RNA removed by digestion with RNAses. Purified DNA may then be obtained by reprecipitation.

After obtaining the high molecular weight DNA, a gene library can be developed using conventional techniques. Conveniently, the high molecular weight DNA is partially digested to produce fragments having an average length of about 5 kbp. Prior to introduce the fragments into cloning vectors, it may be desirable to enrich those fragments in the desired size range, typically from about 4 to 8 kbp. Enrichment may be accomplished by well-known chromatographic methods. See, for example, Hardies and Wells (1976) Proc. Natl. Acad. Sci. USA 73: 3117-21.

The resulting DNA fragments are then inserted into suitable cloning vectors which are introduced into a compatible host. Since the ML gene is of bacterial origin, it is convenient to use a common plasmid vector, such as pBR322 or pBR325, although various phage vectors would also be suitable. Transformants may be selected by a selective marker characteristic of the vector employed. The transformants are further screened for the ability to convert L-malate into L-lactate and the positive colonies cloned to provide a source for the ML gene.

Once the DNA sequence encoding for the malolactic enzyme has been derived from one species, DNA probes can be prepared for isolating polymorphic genes in other species. After creating a gene library from the other species, positive colonies can be identified by nucleic acid hybridization. As an alternative to forming the gene library, the DNA first isolated can be used to construct a probe for isolating mRNA from a second species. The mRNA can then be used to make cDNA which accurately matches the DNA in the genome of the second species.

The malolactic gene of the present invention will usually be incorporated into a vector which enables the gene to replicate within a host and to be transferred between different hosts. Moreover, it is usually desirable that the vector have the ability to vigorously express the polypeptides capable of converting the L-malate into L-lactate. Depending on the contemplated host, the vector may include various regulatory and other regions, always including an origin of replication, usually including one or more promoter regions and markers for the selection of transformants. In general, the vectors will provide regulatory signals for expression, amplification and for a regulated response to a variety of conditions and reagents.

It will often be desirable to provide for replication and regulation capability in both eukaryotic and prokaryotic hosts, which allows for amplification of the vector in prokaryotic hosts, while retaining the ability to be expressed in eukaryotic hosts. Such vectors are referred to as "shuttle vectors."

Various markers may be employed for the selection of transformants, including biocide resistance, particularly to antibiotics such as ampicillin, tetracycline, trimethoprim, chloramphenicol, and penicillin; toxins, such as colicin; and heavy metals, such as mercuric salts. Alternatively, complementation providing an essential nutrient to an auxotrophic host may be employed. Often, different screening markers will be required for both the prokaryotic and eukaryotic hosts, although in some cases both types of organisms may be able to express the same markers.

Hosts which may be employed for the production of the polypeptides of the present invention include unicellular microorganisms, such a prokaryotes, i.e, bacteria; and eukaryotes, such as fungi, including yeasts, algae, protozoa, molds and the like. Specific bacteria which are susceptible to transformation include members of the Enterobacteriacae, such as strains of *Escherichia coli;* Salmonella; Bacillaceae, such as *Bacillus subtilis;* Pneumococcus; Streptococcus; *Haemophilus influenzae,* and yeasts such as Saccharomyces, among others.

The DNA sequences can be introduced directly into the genome of the host or can be first incorporated into a vector which is then introduced into the host. Exemplary methods of direct incorporation include transduction by recombinant phage or cosmids, transfection where specially treated host bacterial cells can be caused to take up naked phage chromosomes, and transformation by calcium precipitation. These methods are well known and need not be described further. Exemplary vectors include plasmids, cosmids, and phages. The availability and use of such vectors are described in Old and Primrose, Principles of Gene Manipulation, Univ. Calif. Press, 1981, Chapters 3–5.

The DNA sequences of the present invention are particularly useful in conferring the ability to perform malolactic fermentation on wine making yeast strains, which are naturally lacking in this ability. Yeasts useful in wine making include strains from the genera Saccharomyces, Torulaspora, and Zygosaccharomyces. Specific species include *S. cervisiae, T. delbrueckii, T. pretoriensis,* and *Z. cidri.*

When the transformation of a wine making yeast strain is contemplated, it is particularly desirable to create a fusion between a yeast promoter and the malolactate gene to increase its expression in yeast. Most simply, this is accomplished by inserting the malolactic gene into a vector which already includes a yeast promoter and a convenient insertion site proximate the yeast promoter. For example, the malolactic gene may be inserted at the Hind III restriction endonuclease site which lies close to the ADH I yeast promoter on the pAAH5 plasmid. The recombinant plasmids can then be used to transform yeast.

To further enhance the malolactate activity of the transformant yeast strains, it may be desirable to fuse subfragments of the DNA sequences isolated as described above. These subfragments may be generated by treatment of the cloned sequence(s) with various restriction endonucleases, and the resulting individual subfragments cloned into pAAH5 as described above. Colonies may then be screened to determine which subfragments provide increased production of the malolactic enzyme.

As a final approach, expression in yeasts can be further improved by locating the malolactic gene very close to the yeast promoter site on the vector. An exonuclease, such as Bal 31, can be used to nibble back the ends of the DNA fragment so that the resulting subfragments are tailored more precisely. That is, the sequence which is inserted has been shortened to eliminate unnecessary bases which act only to increase the distance between the promoter and the structural gene. By performing random digestions, the malolactic gene can be placed near the end of the fragments so that it can be fused to the promoter in a more favorable position.

In addition to fermenting grape juice into wine, the present invention will be useful in fermenting other fruit juices into their alcoholic counterparts. Further examples include, but are not limited to, the fermentation of apple juice into cider, plum juice into plum wine, etc.

The following examples are offered by way of illustration and not by way of limitation.

EXPERIMENTAL

1. Cloning the Malolactic Gene of *Lactobacillus delbrueckii* in *E. coli.*

Transfer of the gene coding for the malolactic enzyme from *Lactobacillus delbrueckii* to yeast was accomplished in two major steps. The gene was first cloned on the plasmid pBR322 in *E. coli* and then inserted into a yeast/ *E. coli* vector for transformation into yeast.

First, the chromosomal DNA of *L. delbrueckii* CUC1 (Kunkee, University of California, Davis, California) was isolated and partially purified. The DNA was isolated using the procedure of Garvie (Int. J. Syst. Bacteriol. (1976) 26:116–122) with the following modifications. Cells were incubated for four hours at 37° C. with gentle shaking in the lysozyme/4-amino salicylate suspension without the pronase. 0.1 mL of 5 mg/mL RNase A per gram of wet-packed cells was then added and incubation continued for four hours. 0.05 mL of 25% sodium dodecyl sulfate per gram of wet-packed cells was added and incubation continued for another four hours. Finally, 0.25 mL chloroform per gram of wet-packed cells were added and incubation continued for 12 more hours. The lysed cells were not treated with 0.5% isopropyl naphthalene sulfonate. Two phenol extractions were used instead of one to deproteinize the viscous solution. Following the chloroform-isoamyl alcohol extraction, 1/30 volume of 5 M NaCl and two volumes ice-cold 95% ethanol were added and the mixture placed on ice for five to ten minutes. The DNA was then spooled out on a glass rod and rinsed by dipping the rod in ice-cold 95% ethanol. The DNA was dissolved in 25 mL fresh SSC buffer, 50 mL 95% ethanol was added and the solution kept on ice for five minutes. The DNA was again spooled out on a glass rod and rinsed by dipping the rod in ice-cold 95% ethanol. The DNA was then dissolved in 2.0 mL of 10 mM Tris-HCl pH 7.6, 1mM EDTA, 5 mM NaCl. The DNA was dialyzed against one liter of this Tris-EDTA-NaCl buffer for six hours, then changed to a fresh liter of the buffer, and dialyzed for another six hours. The *L. delbrueckii* DNA was stored at 4° C. with a drop of chloroform to prevent contamination.

The DNA was considered sufficiently pure when complete cleavage by a battery of three restriction endonucleases was achieved. The enzymes, Bam HI, Hind III, and Sal I, all have unique recognition sites in plasmid pBR322 suitable for cloning. These sites lie downstream from the promoter of the tetracycline resistance gene ($Tc^r$), increasing the probability that DNA cloned into one of them would be transcribed. Because insertion of DNA into any of the sites inactivates the tetracycline resistance gene, clones containing DNA inserts could be selected by screening for $Ap^rTc^s$ transformants.

*L. delbrueckii* chromosomal DNA was partially digested with BAM HI, Hind III, and Sal I in separate experiments and ligated with aliquots of pBR322 DNA digested to completion with the same enzymes. The most complete ligations were achieved with the Sal I digested samples, so most experiments were carried out using this enzyme. The ligated DNA samples were transformed into *E. coli* strain RRI and replica plating was used to identify $Ap^rTc^s$ transformants containing DNA inserts. Groups of fifty transformant colonies were pooled for assay of L-lactate production.

To obtain the plasmids used in subsequent experiments, the partially purified chromosomal DNA was cleaved by SAL I and then ligated to SAL I cleaved pBR322 DNA. To screen for cells transformed by a plasmid, the ligated mixture was spread on plates containing ampicillin. Of the $Ap^r$ colonies that grow on ampicillin plates, only a fraction contained *L. delbrueckii* DNA inserts. To screen for these $Tc^s$ colonies, the ligated mixtures were spread on plates containing fusaric acid in addition to the ampicillin. Fusaric acid had been found to inhibit growth of $Tc^r$ *E. coli* cells harboring the $Tc^r$ gene on a phage vector (Bochner et al. J. Bacteriol. (1980) 143:926-933). They found this fusaric acid selection to be successful with some *E. coli* host strains but not with others.

A series of experiments was performed to test the efficacy of the fusaric acid procedure for selecting tetracycline sensitive clones using the plasmid pBR322 in *E. coli* strain RR1 (Rodriguez, University of California, Davis, California). RR1 cells transformed by plasmids conferring $Ap^r$, $Tc^r$, or both were used to test Luria Broth plates containing varying amounts of ampicillin, fusaric acid, and NaCl. When Luria Broth plates were used containing 40 mg/liter ampicillin, 12 mg/liter fusaric acid, 20 g/liter NaCl, 10 g/liter $NaH_2PO_4 \cdot H_2O$, and 5 mL/liter 20 mm zinc chloride, greater than 90% of the colonies (from a mixture of 50% $Ap^rTc^r$ and 50% $Ap^rTc^s$ cells) that arose were found to be $Ap^rTc^s$. Most of these $Ap^rTc^s$ RRI transformants were found to contain inserts at the Sal I site of the $Tc^r$ gene. Use of these plates containing both ampicillin and fusaric acid allowed for a positive selection of $Ap^rTc^s$ clones.

After screening several thousand pooled colonies, two lactate producing clones were isolated, designated RRI/pSWI and RRI/pSW2. They were discovered amongst 4000 transformants screened from a single *L. delbrueckii*/pBR322 Sal I digestion, ligation, and transformation. Lactate assay results of these two clones and the controls are shown in Table I.

TABLE I
L-Lactate Assays on RRI/pSW1 and RRI/pSW2

| Bacterial Strain Grown in M9-A Without Malate | L-Lactate Produced (μ moles/ 3 mL) | Bacterial Strain Grown In M9-A with 0.3% Malate | L-Lactate Produced (μ moles/ 3 mL) |
|---|---|---|---|
| RRI/pSW1 | 0.07 | RRI/pSW1 | 1.09 |
| RRI/pSW2 | 0.05 | RRI/pSW2 | 0.94 |
| RRI/pBR322 (control) | 0.00 | RRI/pBR322 (control) | 0.00 |
|  |  | *L. delbrueckii* CUC1 (control) | 3.58 |

All cultures were incubated at 37° C. with shaking for 48 hours in M9-A medium with 0% or 0.3% malate.

RRI/pSW1 produced more L-lactate than RRI/pSW2, an amount equal to about 30% of that produced by the *L. delbrueckii* controls.

The L-lactate and L-malate assays herein were all performed on *E. coli* or yeast cultures grown one to five days by the method of Hohorst (Methods of Enzymatic Analysis, Bergmeyer, ed., pp. 266–270, Academic Press, New York, 1963), except that the deproteinized extract assayed was derived from the clear supernatant obtained by pelleting the cells in a Sorval table-top centrifuge (15 minutes of 2000 xg). When screening $Ap^rTc^s$ *E. coli* clones fifty at a time for L-malate to L-lactate conversion, a platinum wire was used to transfer cells from plates to tubes containing 3.0mL of M9-A medium plus 0.3% malate. M9-A medium is M9 medium plus 1.0 mg/liter thiamine, 20 mg/liter L-proline, 20 mg/liter L-leucine, 20 mg/liter L-aspartic acid, and 20 mg/liter ampicillin.

M9-A medium plus 0.1%, 0.3%, 0.6%, or 1.0% malate was used to grow all *E. coli* clones tested for conversion of L-malate to L-lactate. For aerobic growth, cells were transferred using a platinum wire from plates to tubes containing 3.0 mL M9-A medium and grown at 37° C. with shaking for 17 to 48 hours. For anaerobic growth the same procedure was used except 10 mL cultures were inoculated and grown without shaking for five days.

SM-A medium used for all yeast assays contains the following supplements added to one liter of yeast minimal medium: 20 mg arginine, 20 mg histidine (free base), 30 mg isoleucine, 30 mg leucine, 30 mg lysine, 20 mg methionine, 200 mg threonine, 20 mg tryptophane, 20 mg adenine sulfate, and 10 mg uracil. SM-A medium plus 0.1%, 0.3%, 0.6% or 1.0% malate was used to grow all yeast clones tested for conversion of L-malate to L-lactate. For aerobic growth, yeast cells were transferred using a platinum wire from plates to tubes containing 3.0mL of SM-A medium and grown at 30° C. with shaking for 17 to 48 hours. For anaerobic growth the same method was used except 10mL cultures were inoculated and grown without shaking for five days.

*Lactobacillus delbrueckii* CUC1 controls were assayed in the same way except they were grown at 37° C. in M9-L.d. medium which consists of regular M9 medium plus 5.0 g/liter yeast extract and 0.3% malic acid. In this medium, *L. delbruickii* grows very slowly and never achieves the same high cell density as yeast or *E. coli*.

If the malolactic gene of *L. delbrueckii* had been cloned in RRI/pSWI and RRI/pSW2, then the pBR322 plasmids of these two transformants should each contain a piece of *L. delbruickii* DNA of sufficient length to code for the malolactic enzyme. Since the enzyme is known to have a molecular weight of about 120,000 to 150,000 daltons (Schutz and Radler, 1973, 1974, supra), the malolactic gene would have to be at least 3.2 to 4.0 kilobases long. DNA isolated from RRI/pSW1 and RRI/pSW2, cleaved with Sal I, and run on agarose gels, was found to contain identical Sal I inserts of 5.0 kb (sometimes referred to herein as the ML fragment). The new pBR322 plasmid containing the 5.0 kb insert was designated pSW1.

Plasmid isolated from RRI/pSW1 was used to retransform RRI cells to prove that the L-lactate producing character was carried on the plasmid and was not due to some change in the *E. coli* host cell's chromosome. Eight of the newly transformed RRI clones were tested for L-lactate production. Seven of the eight Ap$^r$Tc$^s$ transformants gave significant L-lactate production while controls transformed with pBR322 were all negative (see Table II).

TABLE II

| L-Lactate Assays on RRI Transformed With pSW1 | |
|---|---|
| Bacterial Strain | L-Lactate produced ($\mu$ moles/3 mL) |
| RRI/pBR322 Transformant #1 (control) | 0.00 |
| RRI/pBR322 Transformant #2 (control) | 0.00 |
| *Lactobacillus delbrueckii* CUC1 (control) | 3.61 |
| RRI/pSW1 Transformant #1 | 0.08 |
| #2 | 0.80 |
| #3 | 0.85 |
| #4 | 1.19 |
| #5 | 0.94 |
| #6 | 1.14 |
| #7 | 0.87 |
| #8 | 0.66 |

All cultures were incubated at 37° C. with shaking for 48 hours in M9-A medium with 0.3% malate.

Another experiment was done to demonstrate that RRI/pSW1 cells that had lost the plasmid also lost the ability to produce L-lactate. To cure RRI/pSW1 of its plasmid, the strain was grown to stationary phase in Luria Broth for three serial transfers with no antibiotic selection. After the third transfer, an aliquot of culture was spread on Luria Broth plates, and the resulting colonies were replica plated to Luria Broth with ampicillin and Luria Broth with tetracycline. Colonies that were Ap$^s$Tc$^s$ were presumed to have lost the pSW1 plasmid. Ten such colonies were assayed for L-lactate production in medium with 0.3% L-malate. All were negative. Thus, most transformants containing pSW1 were L-lactate positive, while transformants that had lost pSW1 were always L-lactate negative.

As further proof that the 5.0 kb Sal I fragment was responsible for the ability of cells to produce L-lactate, it was purified from preparative gels and inserted into the Sal I site of another *E. coli* vector (pBR327) at the same location downstream from the Tc$^r$ gene promoter. The new plasmid (pSW3) was transformed into RRI and found to improve L-lactate production over that observed with pSW1 (see Table III).

TABLE III

| L-Lactate Assays on RRI transformed with pSW3 | |
|---|---|
| Bacterial Strain | L-Lactate produced ($\mu$ moles/3 mL) |
| RRI/pSW3a | 1.29 |
| RRI/pSW3b | 1.67 |
| RRI/pSW3c | 1.69 |
| RRI/pSW3d | 1.65 |
| RRI/pSW3e | 1.91 |
| RRI/pBR322 (control) | 0.00 |
| *Lactobacillus delbrueckii* CUC1 (control) | 3.80 |

All cultures were incubated at 37° C. with shaking for 48 hours in M9-A medium with 0.3% malate.

All of these results indicate that the 5.0 kb fragment carries the information required for the production of L-lactate from L-malate in *E. coli* transformed with pSW1 or pSW3.

To prove that the 5.0 kb Sal I fragment was actually *Lactobacillus delbrueckii* DNA, a DNA/DNA hybridization experiment was performed. The purified fragment was radioactively labeled by nick-translation with [$\alpha$-$^{32}$P]CTP using the procedure of Rigby et. al. J. Molc. Biol. (1977) 227–251. The labeled DNA was then hybridized to Sal I cleaved *L. delbrueckii* chromosomal DNA in dry agarose gels. The fragment hybridized to a single 5.0 kilobase band of *L. delbrueckii* DNA but not to control DNA.

The final demonstration that the malolactic gene had been cloned, was to show that a new protein (of the appropriate molecular weight) was encloded by pSW1. *E. coli* maxi-cells transformed with pSW1 were prepared and protein extracts isolated. Proteins encoded by the pSW1 plasmid were radioactively labeled with $^{35}$S-methionine, run on acrylamide gels, and visualized by autoradiography by the method of Sancar et al (1979) J. Bacteriol. 137: 692–693. pSW1 was found to have coded for the appropriate ampicillin resistance gene product: B-lactamase. Bands for this protein of 25, 28 and 30 kilodaltons were observed. The protein encoded by the tetracycline resistance gene was missing, as expected, due to the insertional inactivation of the gene by the fragment. Additionally, a new relatively faint protein band of very high molecular weight appeared that did not appear in any of the control samples. The protein in this band is greater than 100,000 daltons and represents protein coded by the 5.0 kb Sal I fragment.

Thus, all the evidence leads to the conclusion that the malolactic gene of *L. delbrueckii* has indeed been cloned on the *E. coli* plasmid pBR322. Based on the lactate assays and the maxi-cell labeling of plasmid coded proteins, the malolactic gene is expressed in *E. coli*.

2. Transfer of the Malolactic Gene into Yeast

Purified malolactic gene fragment was ligated into the yeast/*E. coli* hybrid vector YRp17 at the Sal I site in the tetracycline resistance gene. The Sal I site in YRp17 is located downstream from the tetracycline promoter as in pBR322 and pBR327. Following transformation of the ligation mixture into *E. coli*, Ap$^r$Tc$^s$ transformants were selected and plasmid DNA isolated. Sal I digests resulted in identification of a clone containing the ML fragment. This clone, along with YRp17 controls which did not contain the ML fragment, were assayed for L-lactate production (see Table IV).

TABLE IV
L-Lactate Assays on RRI Transformed with YRp17/ML Fragment Ligation Mix

| Bacterial Strain | | L-Lactate produced (μ moles/3 mL) |
|---|---|---|
| RRI/YRp17 transformant | #1 | 1.29 |
| | #2 | 0.09 |
| | #3 | 0.08 |
| | #6 | 0.13 |
| | #9 | 0.89 |
| | #10 | 0.07 |
| | #12 | 0.11 |
| RRI (control) | | 0.00 |

All cultures were incubated at 37° C. with shaking for 48 hours in M9-A medium with 0.3% malate.

The only clone found to give a positive lactate assay (RRI/YRp17 transformant #9) contained the ML fragment inserted into the YPp17. The reduced L-lactate production shown by this plasmid in *E. coli* is undoubtedly due to its very large size, resulting in a lower copy number per cell. This plasmid was named ySW1.

ySW1 plasmid DNA was prepared and used to transform yeast strain 2514-10C. ySW1 carries the yeast wild type genes URA3 and TRP1, while 2514-10C is ura3 and trp1. URA3 TRP1 transformants were selected and assayed for lactate production after two days growth. Transformants with ySW1 produced greater amounts of L-lactate than controls transformed with YRp17 (see Table V).

TABLE V
L-Lactate Assays on Yeast Transformed with ySW1

| Yeast or Bacterial Strain | | L-Lactate produced (μ moles/3 mL) |
|---|---|---|
| 2514-10C/ySW1 #9 in: | 0% malate | 0.00 |
| | 0.3% malate | 0.18 |
| | 1.0% malate | 0.45 |
| 2514-10C/ySW1 #19 in: | 0% malate | 0.00 |
| | 0.3% malate | 0.16 |
| | 1.0% malate | 0.45 |
| 2514-10C/YRp17 control in: | 0% malate | 0.00 |
| | 0.3% malate | 0.01 |
| | 1.0% malate | 0.08 |
| *Lactobacillus delbrueckii* CUC1 (control) in: M9-A | 0% malate | 0.00 |
| | 0.3% malate | 1.57 |

All cultures were incubated at 30° C. with shaking for 48 hours in SM-A medium with 0%, 0.3% or 1.0% malate.
*L. delbrueckii* was grown for 48 hours at 37° C. in M9-A medium.

The ySW1 yeast transformants grown in SM-A medium containing one per cent malate gave improved lactate production compared to growth in SM-A medium with 0.3 percent malate. Based on the amount of L-lactate produced, expression of the malolactic gene in yeast is obviously weaker than in *E. coli*, but still significant.

The fast growing ySW1 yeast transformant that gave the greatest lactate production was used to make wine in a trial fermentation. The lab strain 2514-10C transformed with ySW1 carried out an incomplete but satisfactory fermentation. Lactate assays run before and after the fermentation indicated lactate production of 0.83 μmoles/3 mL.

The malolactic gene was transferred to a yeast/*E. coli* vector (pRC3) containing both a 2μ and an ars origin of replication. Again the gene was inserted at the Sal I site of the tetracycline resistance gene downstream from the promoter. The new plasmid (pHWb 2) did not give increased expression in yeast over that observed with ySW1 as measured by lactate assays. However, pHW2 did give better expression in *E. coli* than ySW1 (See Table VI).

TABLE VI
L-Lactate Assays on RRI Transformed with pHW2

| Bacterial Strain | | L-Lactate produced (μ moles/3 mL) |
|---|---|---|
| RRI/pBR327 control in | 0% malate | 0.00 |
| | 1.0% malate | 0.18 |
| RRI/pHW2 #29 in | 0% malate | 0.00 |
| | 1.0% malate | 2.17 |
| RRI/pHW2 #27 in | 0% malate | 0.00 |
| | 1.0% malate | 3.03 |

All cultures were incubated at 37° C. with shaking for 17 hours in M9-A medium with 0% or 1.0% malate.

Since in winemaking the yeast is grown under anaerobic conditions, a series of experiments was designed to test various *E. coli* and yeast strains harboring the malolactic gene for their lactate production under anaerobic conditions. In addition to mimicking conditions used in winemaking, anaerobiosis shuts off the tricarboxylic acid cycle preventing the oxidation of malate. Thus, anaerobic growth conditions should increase the amount of malate available for conversion to lactate in both yeast and *E. coli*. Assays indicated that in *E. coli* much of the malate was used up by the cells after only 17 hours of aerobic growth (see Table VII).

TABLE VII
L-Lactate Assays on RRI Transformed with pBR327 or pHW2

| Growth Medium and Bacterial Strain | | L-malate in Supernatant (μ moles/3 mL) |
|---|---|---|
| M9-A medium | + 0% malate | 1.3 |
| | + 0.3% malate | 56.6 |
| RRI/pBR327 control in | 0% malate | 1.1 |
| | 0.3% malate | 3.0 |
| RRI/pHW2 #27 in | 0% malate | 0.6 |
| | 0.3% malate | 4.0 |

All cultures were incubated at 37° C. with shaking for 17 hours in M9-A medium with 0% or 0.3% malate.

The *E. coli* strain harboring the plasmid pHW2 (with the malolactic gene) used up more malate than the strain with plasmid pBR327 as a control. For example, the M9-A +0.3% malate growth medium had 56.6 μmoles malate/3 mL. The control strain without the ML gene (RRI/pBR327) grown in that medium had 13.0 μmoles malate/3 mL remaining after just 17 hours of growth. The strain with the ML gene (RRI/pHW2 #27) had only 4.0 μmoles malate/3 mL remaining after the same period of growth.

Growing *E. coli* under anaerobic conditions resulted in a much slower utilization of malate in the growth medium (see Table VIII).

TABLE VIII
L-Malate Assays on RRI Transformed with pRC3 or pHW2 Grown Anaerobically

| Growth Medium and Bacterial Strain | | L-Malate in Supernatant (μ moles/3 mL) |
|---|---|---|
| M9-A medium | + 0% malate | 1.3 |
| | + 0.3% malate | 56.6 |
| RRI/pRC3 control in | 0% malate | 0.9 |
| | 0.3% malate | 40.0 |
| RRI/pHW2 #27 in | 0% malate | 0.7 |
| | 0.3% malate | 40.0 |
| RRI/pHW2 #27 in | 0% malate | 0.7 |
| | 0.3% malate | 26.6 |

All cultures were incubated at 37° C. anaerobically for five days in M-9A medium with 0% or 0.3% malate.

As in aerobic growth, the *E. coli* strain carrying the malolactic gene on pHW2 used up more of the malate in anaerobic growth than did the E. coli strain without the malolactic gene.

Since anaerobic growth results in a much slower utilization of malate by E. coli, more malate should be present for conversion to lactate by strains harboring the ML gene. Such strains when grown anaerobically produced more lactate than they had when grown aerobically (See Table IX and Table VI).

TABLE IX

L-Lactate Assays on RRI Transformed with pHW2 Grown Anaerobically

| Bacterial Strain | | L-Lactate Produced (μ moles/3 mL) |
|---|---|---|
| RRI/pBR327 control in | 0% malate | 0.00 |
| | + 0.3% malate | 0.31 |
| RRI/pHW2 #29 in | 0% malate | 0.00 |
| | 0.3% malate | 4.21 |
| RRI/pHW2 #27 in | 0% malate | 0.00 |
| | 0.3% malate | 5.89 |

All cultures were incubated at 37° C. anaerobically for five days in M-9A medium with 0% and 0.3% malate.

Yeast cells grown aerobically also oxidize malate, so anaerobic growth should also increase the concentration of malate available for conversion to lactate in yeast strains harboring the ML gene. When yeast containing the plasmid RC3 (no ML fragment) and yeast with plasmid HW2 (ML fragment) were grown anaerobically the following results were obtained (see Table X).

TABLE X

L-Lactate Assays on Yeast Transformed with pRC3 and pHW2 Grown Anaerobically

| Yeast Strain | | L-Lactate Produced (μ moles/3 mL) |
|---|---|---|
| 2514-10c/pRC3 control in | 0% malate | 0.00 |
| | 0.3% malate | 0.12 |
| | 0.6% malate | 0.24 |
| | 1.0% malate | 0.57 |
| 2514-10c/pHW2 in | 0% malate | 0.00 |
| | 0.3% malate | 0.41 |
| | 0.6% malate | 0.84 |
| | 1.0% malate | 1.35 |
| L. delbrueckii control in SM + | 0% malate | 0.00 |
| | 1.0% malate | 14.2 |

All cultures were incubated at 30° C. anaerobically for five days in SM-A medium with 0%, 0.3%, 0.6%, or 1.0% malate.

When grown anaerobically, yeast with the malolactic gene produced more lactate than when grown aerobically. It should be noted that 2514-10C/pRC3 grown anaerobically also produced small amounts of L-lactate. However, 2514-10C/pHW2 produces about three times more lactate under the same conditions.

3. Vinification Trial

Red grape juice concentrate (Guild Winery, Lodi, California) was diluted approximately five fold with distilled water to give about 3 L of grape juice having 21.8° Brix, a titratable acidity of 0.64% (expressed as tartaric acid) and a pH of 4.1. A sample was frozen for later lactic acid analysis. The juice was treated with 200 mg/L diethyl pyrocarbonate to kill all indigenous yeast and then stored for twenty four hours to dissipate the diethyl pyrocarbonate.

The juice was inoculated with 5 ml of starter culture of yeast strain 2514-10C/ySW1 and incubated at room temperature. The starter culture was prepared by inoculation of 5 ml of sterile (autoclaved) grape juice medium (1:1 dilution of ) grape juice with water, addition of 0.05% yeast extract, and adjustment pH to 4.5) from a slant culture of 2514-10C/ySW1 prepared five days previously. The fermentation was followed by periodic heating of °Brix until there was substantially no change, reaching 6° Brix after thirty three days. After that time another sample was taken for lactic acid analysis.

The cessation of vinification before complete utilization of sugar (at 6° Brix) is typical for fermentation with laboratory strains of yeast and also indicated that only the strain inoculated (2514-10C/ySW1) was present. The vinification could have been completed by addition of a typical wine yeast strain. A lactic acid determination showed formation of 0.83 μmoles lactate per 3 mL fermentation product. This corresponds to a reduction of 1.5% of the malic acid originally present.

Although the foregoing invention has been described in some detail by way of illustration and example for purposes of clarity of understanding, it will be obvious that certain changes and modifications may be practiced within the scope of the appended claims.

What is claimed is:

1. A DNA sequence encoding a polypeptide having ability to convert L-malate into L-lactate, said sequence being derived from Lactobacillus and having a length of about 5 kbp or less.

2. A DNA sequence as in claim 1, wherein the DNA sequence is derived from the chromosomal DNA of *Lactobacillus delbreuekii*.

3. A vector containing the DNA sequence of claim 1 or 2.

4. A vector as in claim 3 which is capable of being stably maintained in a prokaryotic host.

5. A vector as in claim 4 which is capable of being stably maintained in a eukaryotic host.

6. A vector as in claim 3 which is capable of being stably maintained in both prokaryotic and eukaryotic hosts.

7. A method for transforming host cells, said method comprising introducing a DNA sequence as in claims 1 or 2 into the host; where the DNA is capable of replication and expression within the host cells.

8. A host cell transformed in vitro with the DNA sequence of claims 1 or 2 and cells grown from said cell which cells contain said DNA sequence.

9. A eukaryotic cellular host in culture as in claim 8.

10. A yeast host as in claim 8.

11. A prokaryotic host as in claim 8.

* * * * *